United States Patent
Lee et al.

(10) Patent No.: US 8,926,812 B2
(45) Date of Patent: Jan. 6, 2015

(54) CELL-BASED TRANSPARENT SENSOR CAPABLE OF REAL-TIME OPTICAL OBSERVATION OF CELL BEHAVIOR, METHOD FOR MANUFACTURING THE SAME AND MULTI-DETECTION SENSOR CHIP USING THE SAME

(75) Inventors: Nae Eung Lee, Gwacheon-si (KR); Ok Ja Yoon, Seoul (KR); Duck Jin Kim, Suwon-si (KR); Thuy Ngoc Thuy Nguyen, Suwon-si (KR); Il Yung Sohn, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 13/354,490

(22) Filed: Jan. 20, 2012

(65) Prior Publication Data

US 2012/0138458 A1  Jun. 7, 2012

Related U.S. Application Data

(63) Continuation of application No. PCT/KR2010/004822, filed on Jul. 22, 2010.

(30) Foreign Application Priority Data

Jul. 22, 2009 (KR) .......................... 10-2009-0067026
Jul. 22, 2010 (KR) .......................... 10-2010-0071127

(51) Int. Cl.
| | |
|---|---|
| G01N 27/414 | (2006.01) |
| H01L 29/22 | (2006.01) |
| H01L 29/772 | (2006.01) |
| H01L 21/335 | (2006.01) |
| B82Y 30/00 | (2011.01) |

(52) U.S. Cl.
CPC .......... *G01N 27/4145* (2013.01); *G01N 27/414* (2013.01); *G01N 27/4146* (2013.01)
USPC ............ 204/416; 205/789; 257/253; 204/435

(58) Field of Classification Search
CPC ......................... G01N 27/414; G01N 27/4146
USPC ................... 257/253; 205/789; 204/416, 435
See application file for complete search history.

(56) References Cited

U.S. PATENT DOCUMENTS

| 4,874,500 A | * | 10/1989 | Madou et al. ................. 204/412 |
| 5,911,862 A | * | 6/1999 | Chan ............................. 204/418 |
| 6,914,279 B2 | * | 7/2005 | Lu et al. ........................... 506/39 |
| 2007/0132043 A1 | * | 6/2007 | Bradley et al. ................ 257/414 |

OTHER PUBLICATIONS

Wolf et al. (BioMEMS Microsystems vol. 16, 2006, pp. 269-307).*

(Continued)

*Primary Examiner* — Luan Van
*Assistant Examiner* — Steven Rosenwald
(74) *Attorney, Agent, or Firm* — NSIP Law

(57) ABSTRACT

The present invention relates to a cell-based transparent sensor capable of the real-time optical observation of cell behavior, to a method for manufacturing same, and to a multi-detection sensor chip using same. More particularly, the present invention relates to a cell-based transparent sensor capable of the real-time optical observation of cell behavior, to a method for manufacturing same, and to a multi-detection sensor chip using same, wherein the sensor can sense the ionic concentration of an electrolyte in accordance with the variation in the metabolic activity of cells using an ion-selective field effect transistor (ISFET) sensor and an electrochemical sensor, and the sensor is made of a transparent material which enables real-time observations of optical phenomenon for measurement of cell behavior.

15 Claims, 4 Drawing Sheets

(56) References Cited

OTHER PUBLICATIONS

Mitsubayashi et al. (Anal. Sci., V17, 2001, supplement, i773-i776).*
Wiest et al. (Chimia 59, 2005, 243-246).*
Zhang et al. (Appl. Phys. Lett. 92, 243307, 2008).*
Chang et al. (Appl. Phys. Lett. 91, 083502, 2007).*
Maminska (Sensors and Actuators B, 115, 2006, 552-557).*
Ye et al. (J. Electroanal. Chem., 562, 2004, 241-246).*

* cited by examiner

CELL-BASED TRANSPARENT SENSOR CAPABLE OF REAL-TIME OPTICAL OBSERVATION OF CELL BEHAVIOR, METHOD FOR MANUFACTURING THE SAME AND MULTI-DETECTION SENSOR CHIP USING THE SAME

CROSS-REFERENCE TO RELATED APPLICATIONS

This application is a continuation of International Patent Application No. PCT/KR2010/004822, filed on Jul. 22, 2010, which claims the benefit of Korean Patent Application Nos. 10-2009-0067026 and 10-2010-0071127 filed on Jul. 22, 2009 and Jul. 22, 2010, respectively, the entire disclosures of which are incorporated herein by reference for all purposes.

BACKGROUND

1. Field

The following description relates to a cell-based transparent sensor and a method for manufacturing the same. The description further relates to a cell-based transparent sensor capable of the real-time optical observation of cell behavior. The cell-based transparent sensor may be configured to detect an ionic concentration of an electrolyte that corresponds to a variation in the metabolic activity of cells by using an ion-selective field effect transistor (ISFET) sensor and an electrochemical sensor. The cell-based transparent sensor may be formed of a transparent material to allow the optical observation and measurement of cell behavior in real-time. The following description also relates to a method for manufacturing such a sensor, and a multi-detection sensor chip that uses the same.

2. Description of Related Art

One type of sensor among the various sensors that are used for detecting biomolecules with an electrical signal is a transistor-based biosensor that includes a transistor. Such a transistor-based biosensor may be manufactured using a semiconductor fabrication process. Transistor-based biosensors are typically characterized by a rapid switching of an electrical signal and a simple combination of integrated circuit (hereinafter, referred to as an "IC") and a micro-electro mechanical system (Hereinafter, referred to as a "MEMS"). Thus, many studies are being conducted on the transistor-based biosensor.

U.S. Pat. No. 4,238,757 is the original patent relating to the detection of a biological response using a field effect transistor (hereinafter, referred to as a "FET"). This patent relates to a biosensor for detecting an antigen-antibody reaction by sending a current change in a semiconductor inversion layer that occurs due to a change in the surface charge concentration. That is, this patent relates specifically to the detection of protein molecules among the various biomolecules that exist in nature.

SUMMARY

In one general aspect, there is provided a cell-based transparent sensor. The cell-based transparent senor may include a transparent substrate, an ion-selective field effect transistor sensor disposed on the transparent substrate, and an oxygen detection electrochemical sensor disposed on the transparent substrate in parallel to the ion-selective field effect transistor sensor. The ion-selective field effect transistor sensor may include transparent drain and source electrodes, a transparent semiconductor layer disposed on the transparent drain and source electrodes, a transparent ion-sensitive insulator detection layer disposed on the transparent substrate, transparent ion-selective membranes disposed on the transparent ion-sensitive insulator detection layer, and a reference electrode disposed between the transparent ion-selective membranes. The oxygen detection electrochemical sensor may include a transparent counter electrode, the reference electrode, and a transparent working electrode which are disposed on the transparent ion-sensitive insulator detection layer.

Each of the transparent drain and source electrodes may be formed of a transparent metal oxide, a conductive polymer, a nano material, or a mixture thereof. The transparent metal oxide may include a transparent metal oxide selected from the group consisting of ITO, ZnO, IZO, AZO, ZTO, and $TiO_2$.

The conductive polymer may be selected from the group consisting of polyaniline, polypyrrole, and poly(3,4-ethylenedioxythiophene). The nano material for the transparent drain and source electrodes may be selected from the group consisting of graphene, carbon nanotube (CNT), and nanowire.

The transparent semiconductor layer may be formed of a semiconductor material selected from the group consisting of pentacene, ZnO, and InGaZnO.

The transparent ion-sensitive insulator detection layer may be manufactured by depositing a material selected from the group consisting of $Ta_2O_5$, $Al_2O_3$, $Si_3N_4$, and $SiO_2$ on the transparent substrate. Each of the transparent ion-selective membranes may be selected from the group consisting of a pH detection membrane, a $Ca^{2+}$ detection membrane, a $K^+$ detection membrane, a $Na^+$ detection membrane, and a $pCO_2$ detection membrane.

In the transparent ion-selective membranes, the pH detection membrane may be coated with a material selected from the group consisting of tridodecylamine, nonadecylpyridine, octadecylisonicotinate, dipropylaminoazobenzene derivative, nile blue derivative, o-nitrophenyl octyl ether, and potassium tetrakis(p-chlorophenyl)borate (KTFPB). The $Ca^{2+}$ detection membrane may be coated with a material selected from the group consisting of ETH 1001™ ((−)-(R,R)—N,N'-[bis(11-ethoxycarbonyl)undecyl-N,N',4,5-tetramethyl]-3,6-dioxaoctancediamide), ETH 129™ (N,N,N',N'-tetracyclohexyl-3-oxapentanediamide), K23EI (4,16-Di-N-octadecylcarbamoyl-3-oxabutyryl-1,7,10,13,19-pentaoxa-4,16-diazacycloheneicosane), bis(phenylazonaphthyl)triether, and di(octylphenyl)phosphoric acid. The $K^+$ detection membrane may be coated with a material selected from the group consisting of Bis(benzo-15-crown-5), Calix[4]arenecrown-5, functionalized polysiloxanes, KTTFPB™ (potassium tetrakis [3,5]-bis(trifluoromethyl)phenylborate), and poly-HEMA. The $Na^+$ detection membrane may be coated with a material selected from the group consisting of 16-Crown-5 and Calix[4]arenecrown-4. The $pCO_2$ detection membrane may be coated with a material selected from the group consisting of silicon rubber, microporous polypropylene, and microporous Teflon.

Each of the transparent counter electrode and the transparent working electrode of the oxygen detection electrochemical sensor may be formed of one or more mixtures selected from the group consisting of carbon nanotube, graphene/hydroxyapatite, bromoform, and polyethylene. The reference electrode may include a silver-silver chloride reference electrode in which silver is deposited and chlorinated. A polyvinylchloride (PVC) membrane may be disposed on the silver-silver chloride reference electrode. The transparent substrate may include a glass substrate or a transparent plastic substrate.

In the cell-based transparent sensor, a well and scaffold for culturing cells may be disposed on the cell-based transparent sensor.

In another general aspect, there is provided a method for manufacturing a cell-based transparent sensor comprising an ion-selective field effect transistor sensor and an oxygen detection electrochemical sensor which are disposed in parallel on a transparent substrate. The method may involve forming the ion-selective field effect transistor sensor on the transparent substrate (Step 1), forming the oxygen detection electrochemical sensor in parallel to the ion-selective field effect transistor sensor after the ion-selective field effect transistor sensor is formed in the Step 1 (Step 2).

The method may further involve forming a well and scaffold for culturing cells on the ion-selective field effect transistor sensor and the oxygen detection electrochemical sensor after the oxygen detection electrochemical sensor is formed.

The ion-selective field effect transistor sensor may be manufactured by: forming transparent drain and source electrodes to form a transparent semiconductor layer between the transparent drain and source electrodes; coating a transparent ion-sensitive insulator detection layer on the transparent substrate; and forming transparent ion-selective membranes and a reference electrode on the transparent ion-sensitive insulator detection layer.

The oxygen detection electrochemical sensor may be manufactured by: forming a transparent counter electrode, a reference electrode, and a transparent working electrode on a transparent ion-sensitive insulator detection layer, which is formed when the ion-selective field effect transistor sensor is manufactured, in parallel to the ion-selective field effect transistor sensor; and forming a oxygen detection membrane on the working electrode.

Each of the transparent drain and source electrodes may be formed of a transparent metal oxide, a conductive polymer, a nano material, or a mixture thereof. The transparent metal oxide may be selected from the group consisting of ITO, ZnO, IZO, AZO, ZTO, and $TiO_2$. The conductive polymer may be selected from the group consisting of polyaniline, polypyrrole, and poly(3,4-ethylenedioxythiophene). The nano material may be selected from the group consisting of graphene, carbon nanotube (CNT), and nanowire.

The transparent semiconductor layer may include a semiconductor material selected from the group consisting of pentacene, ZnO, and InGaZnO.

The transparent ion-sensitive insulator detection layer may be manufactured by depositing a material selected from the group consisting of $Ta_2O_5$, $Al_2O_3$, $Si_3N_4$, and $SiO_2$ on the transparent substrate. Each of the transparent ion-selective membranes may be selected from the group consisting of a pH detection membrane, a $Ca^{2+}$ detection membrane, a $K^+$ detection membrane, a $Na^+$ detection membrane, and a $pCO_2$ detection membrane.

In the transparent ion-selective membranes according to one example, the pH detection membrane may be coated with a material selected from the group consisting of tridodecylamine, nonadecylpyridine, octadecylisonicotinate, dipropylaminoazobenzene derivative, nile blue derivative, o-nitrophenyl octyl ether, and potassium tetrakis(p-chlorophenyl) borate (KTFPB). The $Ca^{2+}$ detection membrane may be coated with a material selected from the group consisting of ETH 1001™ ((-)-(R,R)—N,N'-[bis(11-ethoxycarbonyl)undecyl-N,N',4,5-tetramethyl]-3,6-dioxaoctancediamide), ETH 129™ (N,N,N',N'-tetracyclohexyl-3-oxapentanediamide), K23EI (4,16-Di-N-octadecylcarbamoyl-3-oxabutyryl-1,7,10,13,19-pentaoxa-4,16-diazacycloheneicosane), bis(phenylazonaphthyl)tri-ether, and di(octylphenyl)phosphoric acid. The $K^+$ detection membrane may be coated with a material selected from the group consisting of Bis(benzo-15-crown-5), Calix[4]arenecrown-5, functionalized polysiloxanes, KTTFPB™ (potassium tetrakis [3,5]-bis(trifluoromethyl)phenylborate), and poly-HEMA. The $Na^+$ detection membrane may be coated with a material selected from the group consisting of 16-Crown-5 and Calix[4]arenecrown-4; and the $pCO_2$ detection membrane is coated with a material selected from the group consisting of silicon rubber, microporous polypropylene, and microporous Teflon.

Each of the transparent counter electrode and the transparent working electrode of the oxygen detection electrochemical sensor may be formed of one or more mixtures selected from the group consisting of carbon nanotube, graphene/hydroxyapatite, bromoform, and polyethylene, the reference electrode comprises a silver-silver chloride reference electrode in which silver is deposited and chlorinated, and a polyvinylchloride (PVC) membrane is disposed on the silver-silver chloride reference electrode.

In yet another aspect, there is provided a multi-detection sensor chip comprising a cell-based transparent sensor and a read-out conditioning circuit to optically and electrochemically measure cell behavior. The multi-detection sensor chip may include a transparent substrate, an ion-selective field effect transistor sensor disposed on the transparent substrate, and an oxygen detection electrochemical sensor disposed parallel to the ion-selective field effect transistor sensor.

The read-out conditioning circuit may condition an electrical signal transmitted from the cell-based transparent sensor. The read-out conditioning circuit may be electrically connected to a signal processing processor, a controller, and a data display.

In another aspect, there is provided a cell-based transparent sensor including a transparent substrate, a first ion-selective field effect transistor sensor and a first oxygen detection electrochemical sensor disposed on the transparent substrate, and a second ion-selective field effect transistor sensor and a second oxygen electrochemical sensor disposed on the transparent substrate.

In the cell-based transparent sensor, the first ion-selective field effect transistor sensor may be disposed parallel to a first oxygen detection electrochemical sensor disposed in a first reaction area of the transparent substrate, and the second ion-selective field effect transistor sensor may be disposed parallel to the second oxygen electrochemical sensor in a second reaction area of the transparent substrate.

The first and second ion-selective field effect transistor sensor may include transparent drain and source electrodes, a transparent semiconductor layer disposed on the transparent drain and source electrodes, a transparent ion-sensitive insulator detection layer disposed on the transparent substrate, transparent ion-selective membranes disposed on the transparent ion-sensitive insulator detection layer, and a reference electrode disposed between the transparent ion-selective membranes. The first and second oxygen detection electrochemical sensors may include a transparent counter electrode, the reference electrode, and a transparent working electrode which are disposed on the transparent ion-sensitive insulator detection layer.

Other features and aspects may be apparent from the following detailed description, the drawings, and the claims.

Figure 1:
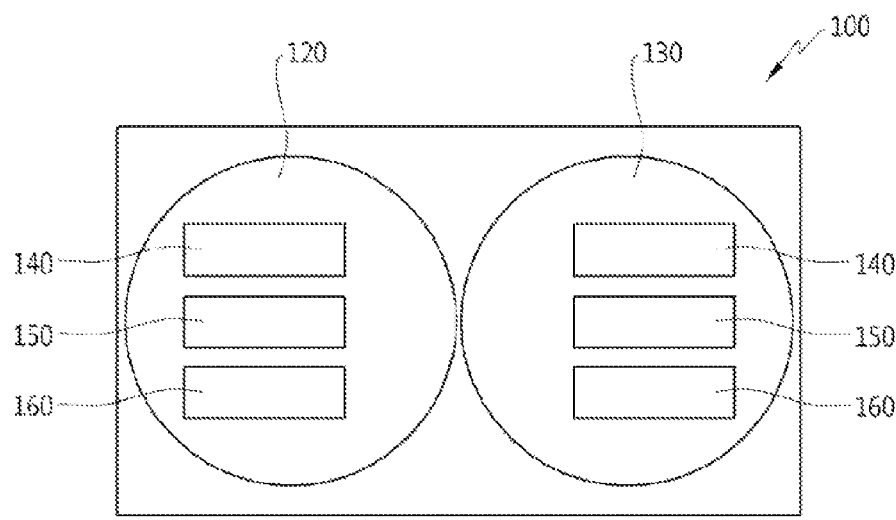
FIG. 1 is a schematic diagram illustrating an example of a cell-based transparent sensor according to a general aspect.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, compositions and/or systems described herein. Accordingly, various changes, modifications, and equivalents of the systems, apparatuses, compositions and/or methods described herein will be suggested to those of ordinary skill in the art. Also, descriptions of well-known functions and constructions may be omitted for increased clarity and conciseness.

As described above, a biosensor using a FET is characterized by low costs, high-speed sensing, and a simple combination of IC/MEMS process in comparison to conventional devices.

Such an ion-selective field effect transistor (ISFET) sensor applies a voltage $V_{DS}$ between a drain and a source and a voltage $V_{GS}$ between a gate and the source using three electrodes, i.e., a source electrode, a gate electrode, and a drain electrode, to measure a variation in a drain current IDS due to the accumulation and depletion of carriers within a semiconductor according to a variation in a surface potential depending on an ion concentration accumulated onto a gate insulation layer. Here, the ISFET sensor may selectively and simultaneously detect specific ions, molecules and their concentrations such as $H^+$ (pH), $Ca^{2+}$, $K^+$, $Na^+$, and $CO_2$ ($pCO_2$). Also, an electrochemical sensor detects an oxygen ($O_2$) ion concentration due to a variation in the current and impedance generated by an oxidation-reduction reaction of an electrolyte.

The ISFET sensor was invented by Bergveld in the 1970's, and thereafter, many studies are being conducted on ISFET sensors to realize their full potentials. Recently, studies about ISFET sensors as chemical sensors capable of measuring gas states such as gas sensors as well as ion sensors are being actively conducted. Such an ISFET sensor is a type of transistor. An insulated gate field effect transistor (IGFET) and an ion sensor may be integrated together in order to manufacture the ISFET sensor. Since the ISFET sensor is an ideal detector in which an electric potential is measured by an insulation layer to measure an electric potential difference, an output impedance may be minimally reduced by a feed-back circuit. Thus, the ISFET sensor may serve as a microminiaturized, low-output impedance ion sensor that is completely different from existing ion sensors. According to an operation principle of the ISFET sensor, since an electrochemical potential difference at an interface between a solution and a detection membrane is changed according to an ion concentration within the solution, the electric potential change causes a change in an effective gate voltage (VG) according to a change in a threshold voltage (VT). As a result, channel conductivity may be changed by an electric field effect to cause a change in a drain current. Thus, the ISFET sensor may measure a variation in the drain current to detect a variation in a specific ion concentration within the solution. Since an ion detection membrane selectively sensitive to a specific ion is provided in the ISFET sensor, a sensor capable of sensing various ions may be manufactured. Also, a voltammetry that is a kind of amperometry using an electrochemical sensor was proposed by Clark in the 1970's. Thereafter, electrodes for detecting oxygen and hydrogen peroxide are being developed.

As the development of biosensor progresses, micro components that were difficult to measure due to their microminiaturized size in the past is becoming easier to measure in recent years. Specifically, biosensors in which living body-related materials having a molecular recognition function such as enzymes, antibodies, cells, and microorganisms, and various devices such as electric devices are combined together are being developed. However, it may be difficult to optically measure the living body-related materials in a cell-based device due to the opaqueness of the device. Thus, technologies for measuring the cell behavior phenomenon have not yet been reported.

The following description describes a cell-based transparent sensor that is configured to detect various ions based on a biological change inside a cell and to optically measure a cell behavior phenomenon because the cell-based transparent sensor is formed of a transparent material. Also described herein is a method for manufacturing such a cell-based transparent sensor.

Also described herein is a multi-detection sensor chip that includes a cell-based transparent sensor and includes a read-out conditioning circuit that is electrically connected to the cell-based transparent sensor in order to optically and electrochemically measure a cell behavior phenomenon.

In accordance with one example, a cell-based transparent sensor may include: a transparent substrate; an ion-selective field effect transistor sensor disposed on the transparent substrate; and an oxygen detection electrochemical sensor disposed on the transparent substrate in parallel to the ion-selective field effect transistor sensor, wherein the ion-selective field effect transistor sensor includes: transparent drain and source electrodes; transparent semiconductor layer disposed on the transparent drain and source electrodes; a transparent ion-sensitive insulator detection layer disposed on the transparent substrate; transparent ion-selective membranes disposed on the transparent ion-sensitive insulator detection layer; and a reference electrode disposed between the transparent ion-selective membranes, and the oxygen detection electrochemical sensor includes a transparent counter electrode, the reference electrode, and a transparent working electrode which are disposed on the transparent ion-sensitive insulator detection layer.

In accordance with another example, a method for manufacturing a cell-based transparent sensor including an ion-selective field effect transistor sensor and an oxygen detection electrochemical sensor which are disposed in parallel on a transparent substrate includes: forming the ion-selective field effect transistor sensor on the transparent substrate (Step 1); and forming the oxygen detection electrochemical sensor in parallel to the ion-selective field effect transistor sensor after the ion-selective field effect transistor sensor is formed in the Step 1 (Step 2).

In accordance with yet another example, a multi-detection sensor chip including a cell-based transparent sensor and a read-out conditioning circuit to optically and electrochemically measure cell behavior includes: a transparent substrate; an ion-selective field effect transistor sensor disposed on the transparent substrate; and an oxygen detection electrochemical sensor disposed parallel to the ion-selective field effect transistor sensor, wherein the read-out conditioning circuit conditions an electrical signal transmitted from the cell-based transparent sensor.

Each of the transparent drain and source electrodes may be formed of a transparent metal oxide, a conductive polymer, a nano material, or a mixture thereof. The transparent metal oxide may include one of ITO, ZnO, IZO, AZO, ZTO, and $TiO_2$.

The conductive polymer may include one of polyaniline, polypyrrole, and poly(3,4-ethylenedioxythiophene), and the nano material may include one of graphene, carbon nanotube (CNT), and nanowire.

Each of the transparent ion-selective membranes may include one of a pH detection membrane, a $Ca^{2+}$ detection membrane, a $K^+$ detection membrane, a $Na^+$ detection membrane, and a $pCO_2$ detection membrane.

The cell-based transparent sensor may be configured to allow the optical observation of cell behaviors in real-time because the cell-based transparent sensor is formed of a transparent material. Also, a change in cell properties due to environments may be confirmed according to a variation in a current value generated by a concentration gradient change of pH ($H^+$), $K^+$, $Ca^{2+}$, $Na^+$, $pCO_2$ ($CO_2$), $O^{2-}$ ($O_2$) and the like, depending on a cell metabolism change in the oxygen detection electrochemical sensor and the ISFET sensor. Also, the cell-based transparent sensor according to the present disclosure may obtain accurate information with respect to a variation in biological activities of actual cells, reaction mechanisms, and reaction responses against foreign substances. Furthermore, the cell-based transparent sensor may be directly applied to a performance and toxicity evaluation of a new medicine, environmental monitoring, clinical diagnosis, and the like. Also, since the present disclosure describes the multi-detection sensor chip including the cell-based transparent sensor and the read-out conditioning circuit electrically connected to the cell-based transparent sensor, the cell behavior may be optically observed in real-time and signals generated in the cell-based transparent sensor may be electrochemically detected to improve detection reliability.

Also described herein is an example of a cell-based transparent sensor including: a transparent substrate; an ion-selective field effect transistor sensor disposed on the transparent substrate; and an oxygen detection electrochemical sensor disposed on the transparent substrate in parallel to the ion-selective field effect transistor sensor, wherein the ion-selective field effect transistor sensor includes: transparent drain and source electrodes; a transparent semiconductor layer disposed on the transparent drain and source electrodes; a transparent ion-sensitive insulator detection layer disposed on the transparent substrate; transparent ion-selective membranes disposed on the transparent ion-sensitive insulator detection layer; and a reference electrode disposed between the transparent ion-selective membranes, and the oxygen detection electrochemical sensor includes a transparent counter electrode, the reference electrode, and a transparent working electrode which are disposed on the transparent ion-sensitive insulator detection layer.

Figure 2:
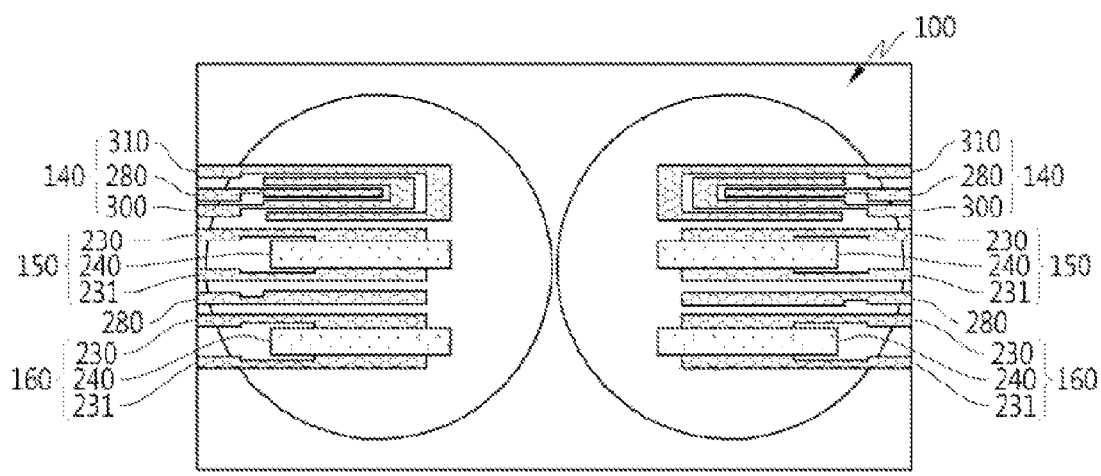
FIG. 2 is a view illustrating components of an electrochemical sensor and an ion-selective field effect transistor sensor in an example of a cell-based transparent sensor.

FIG. 1 illustrates an example of a cell-based transparent sensor. FIG. 2 illustrates components of an electrochemical sensor for detecting oxygen and an ion-selective field effect transistor (ISFET) sensor in the cell-based transparent sensor in accordance with another example.

Referring to FIGS. 1 and 2, a cell-based transparent sensor 100 according to one general aspect may include an electrochemical sensor 140 for detecting oxygen (hereinafter, referred to as an "oxygen detection electrochemical sensor 140") and ISFET sensors 150 and 160. Here, the oxygen detection electrochemical sensor 140 and the ISEFT sensors 150 and 160 may be disposed on both sides of an actual measurement sample chamber 120 and a control sample chamber 130 as illustrated in FIG. 1. Thus, the cell-based transparent sensor 100 may detect ions and optically measure the ions according to a cell response.

Hereinafter, the cell-based transparent sensor 100 according to one example will be described with reference to FIGS. 1 and 2.

The ISFET sensors 150 and 160 may be manufactured by successively arranging a transparent drain electrode 230, a transparent source electrode 231, a transparent semiconductor layer 240, a transparent ion-sensitive insulator detection layer 250, a reference electrode 280, and transparent ion-selective membranes 260 and 270 on a transparent substrate 210.

The cell-based transparent sensor 100 may be formed of a transparent material to detect two or more ions and optically measure a cell behavior phenomenon.

In the cell-based transparent sensor 100, a transparent electrode layer may be disposed on the transparent substrate and then patterned to manufacture the transparent drain electrode 230 and the transparent source electrode 231 so that the cell behavior phenomenon is optically measured. Also, two or more ISFET sensors 150 and 160 may be provided on the transparent drain and source electrodes 230 and 231 so that two or more ions (or molecules) of $H^+$ (pH), $Ca^{2+}$, $K^+$, $Na^+$, $CO_2$ ($pCO_2$) are selectively and simultaneously detected. Also, the oxygen detection electrochemical sensor 140 and the ISFET sensors 150 and 160 are disposed in parallel so that oxygen ions may be detected.

A glass substrate or a transparent plastic substrate may be used as the transparent substrate 210.

The transparent drain and source electrodes 230 and 231 disposed on the transparent substrate 210 may be manufactured by depositing a transparent metal oxide, a conductive polymer, a nano material, or a mixture thereof on the transparent substrate 210. Since the drain and source electrodes 230 and 231 are transparent, the cell behavior phenomenon may be optically measured.

The transparent metal oxide may include metal oxide-based materials such as ITO, $SnO_2$, IZO, AZO, and $TiO_2$, but the material is not limited thereto. For example, various conductive metal oxides having transparency may be used as the transparent metal oxide.

Examples of conductive polymers include polyaniline, polypyrrole, poly(3,4-ethylenedioxythiophene), and the like. Examples of nano materials include graphene, carbon nanotube (CNT), nanowire, and the like. Also, nano composites of the nano materials and the conductive polymers may be used.

In the ISFET sensors 150 and 160, the transparent semiconductor layer 240 may be disposed between the transparent drain and source electrodes 230 and 231, and the transparent ion-sensitive insulator detection layer 250 may be disposed on the transparent substrate 210. Thereafter, the transparent ion-selective membranes 260 and 270 may be disposed on the transparent ion-sensitive insulator detection layer 250, and the reference electrode 280 may be disposed between the transparent ion-selective membranes 260 and 270.

The transparent semiconductor layer 240 may be formed of an organic semiconductor such as pentacene. In another example, the transparent semiconductor layer 240 may be manufactured by depositing one of inorganic transparent oxide semiconductor materials such as ZnO, ZnSnO, GaZnO, and InGaZnO between the transparent drain and source electrodes 230 and 231. Particularly, the transparent semiconductor layer 240 may be formed of an organic semiconductor, i.e., one of P-type oligomers such as $Me_2$-pentacene, bis-Benzodithiophene (bis-BDT), bis-thiophene dimer (bis-TDT), sexithiphene (6T), Hexyl-substituted thiophene oligomers (DH-6T), mixed thiophene-phenylene oligomers (dH-PPTPP, dH-PTTP), anthradithiophene (ADT), rubrene, and copper phthalocyanine (PcCu), polymers such as poly(3-hexylthiophene) (P3HT), polyquaterthiophenes (PQTs), poly[9,9-dioctylfluorene-co-bithiophene] (F8T2), 99,9-dialkylfluorene-alt-triarylamine (TFB), carbazole (PCB), and polytriarylamines (PTAA), or N-type oligomers such as quinoimethane terthiophene (QM3T), perfluoroarene-thiophene oligomers (FTTTTF), naphthalene carbodiimide (NTCDI) monomer, and fullerenes ($C_{60}$).

In the ISFET sensors 150 and 160 of the cell-based transparent sensor 100 according to one example, the transparent ion-sensitive insulator detection layer 250 may be first disposed. Thereafter, the transparent ion-selective membranes 260 and 270, through which an ion to be detected within an electrolyte selectively passes to accumulate the ion on a surface of the transparent ion-sensitive insulator detection layer 250, may be successively disposed to detect $H^+$ (pH), $CO_2$ ($pCO_2$), $Ca^{2+}$, $K^+$, $Na^+$ ions and the like.

The transparent ion-sensitive insulator detection layer 250 may be manufactured by depositing a material selected from the group consisting of $Ta_2O_5$, $Al_2O_3$, $Si_3N_4$, and $SiO_2$. Alternatively, a polymer material may be prepared first, and then $Ta_2O_5$, $Al_2O_3$, $Si_3N_4$, and $SiO_2$ may be deposited on the polymer material to manufacture the transparent ion-sensitive insulator detection layer 250 having a multi-layered structure.

The transparent ion-selective membranes 260 and 270 may selectively include one of a pH detection membrane, a $Ca^{2+}$ detection membrane, a $K^+$ detection membrane, a $Na^+$ detection membrane, or a $pCO_2$ detection membrane according to an ion to be detected.

The pH detection membrane may be coated with a material selected from the group consisting of tridodecylamine, nonadecylpyridine, octadecylisonicotinate, dipropylaminoazobenzene derivative, nile blue derivative, o-nitrophenyl octyl ether, and potassium tetrakis(p-chlorophenyl)borate (KTFPB). The $Ca^{2+}$ detection membrane may be coated with a material selected from the group consisting of ETH 1001™ ((−)-(R,R)—N,N'-[bis(11-ethoxycarbonyl)undecyl-N,N',4,5-tetramethyl]-3,6-dioxaoctancediamide), ETH 129™ (N,N,N',N'-tetracyclohexyl-3-oxapentanediamide), K23EI (4,16-Di-N-octadecylcarbamoyl-3-oxabutyryl-1,7,10,13,19-pentaoxa-4,16-diazacycloheneicosane), bis(phenylazonaphthyl)tri-ether, and di(octylphenyl)phosphoric acid.

The $K^+$ detection membrane may be coated with a material selected from the group consisting of Bis(benzo-15-crown-5), Calix[4]arenecrown-5, functionalized polysiloxanes, KTTFPB™ (potassium tetrakis [3,5]-bis(trifluoromethyl)phenylborate), and poly-HEMA.

The $Na^+$ detection membrane may be coated with a material selected from the group consisting of 16-Crown-5 and Calix[4]arenecrown-5.

The $pCO_2$ detection membrane may be coated with a material selected from the group consisting of silicon rubber, microporous polypropylene, and microporous Teflon. However, the coating materials are not limited to the above-described materials. For example, materials commonly used in the technical field may be used in another example.

The oxygen detection electrochemical sensor 140 may include a transparent counter electrode 310, the reference electrode 280, and a transparent working electrode 300. The transparent counter electrode 310, the reference electrode 280, and the transparent working electrode 300 may be disposed in parallel on the ISFET sensors 150 and 160 and the transparent ion-sensitive insulator detection layer 250.

The transparent counter electrode 310 and the transparent working electrode 300 of the oxygen detection electrochemical sensor 140 may be manufactured using one or two or more mixtures selected from the group consisting of carbon nanotube, graphene/hydroxyapatite, bromoform, and polyethylene.

The reference electrode 280 of the oxygen detection electrochemical sensor 140 may be a silver-silver chloride reference electrode in which silver is deposited and chlorinated. A polyvinylchloride (PVC) membrane may be disposed on the silver-silver chloride reference electrode to improve the stability of the reference electrode.

Figure 4:
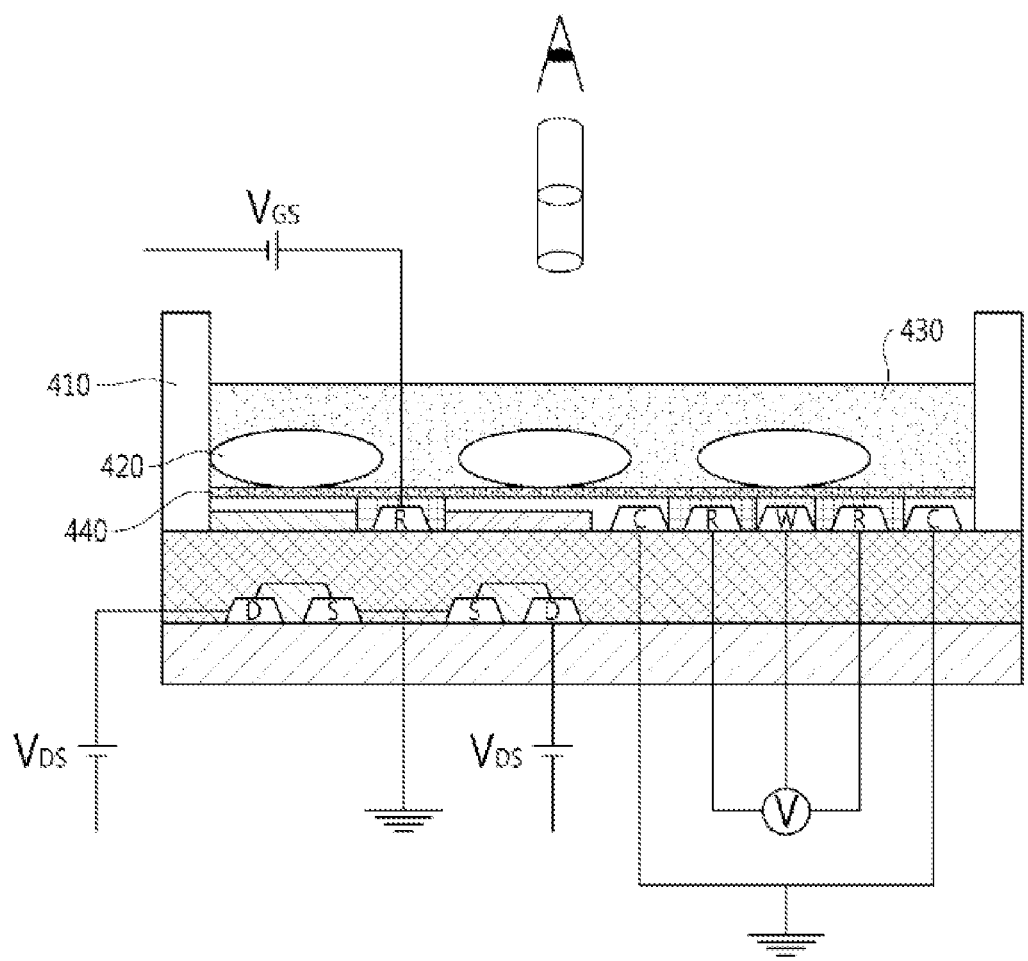
FIG. 4 is a cross-sectional view illustrating a cell-based transparent sensor manufactured according to a general aspect.

Referring to FIG. 4, in the cell-based transparent sensor 100 according to one example, a scaffold 440 for culturing cells may be disposed on the ISFET sensors 150 and 160 and the oxygen detection electrochemical sensor 140. Also, a well 410 may be disposed on the outside of the cell-based transparent sensor 100 to measure the cell culture and the cell behavior phenomenon.

Also, described herein is a method for manufacturing a cell-based transparent sensor including an ISFET sensor and an oxygen detection electrochemical sensor which are disposed in parallel on a transparent substrate. The method may involve: forming the ISFET sensor on the transparent substrate (Step 1); and forming the oxygen detection electrochemical sensor in parallel to the ISFET sensor after the ISFET sensor is formed in the Step 1 (Step 2).

Figure 3:
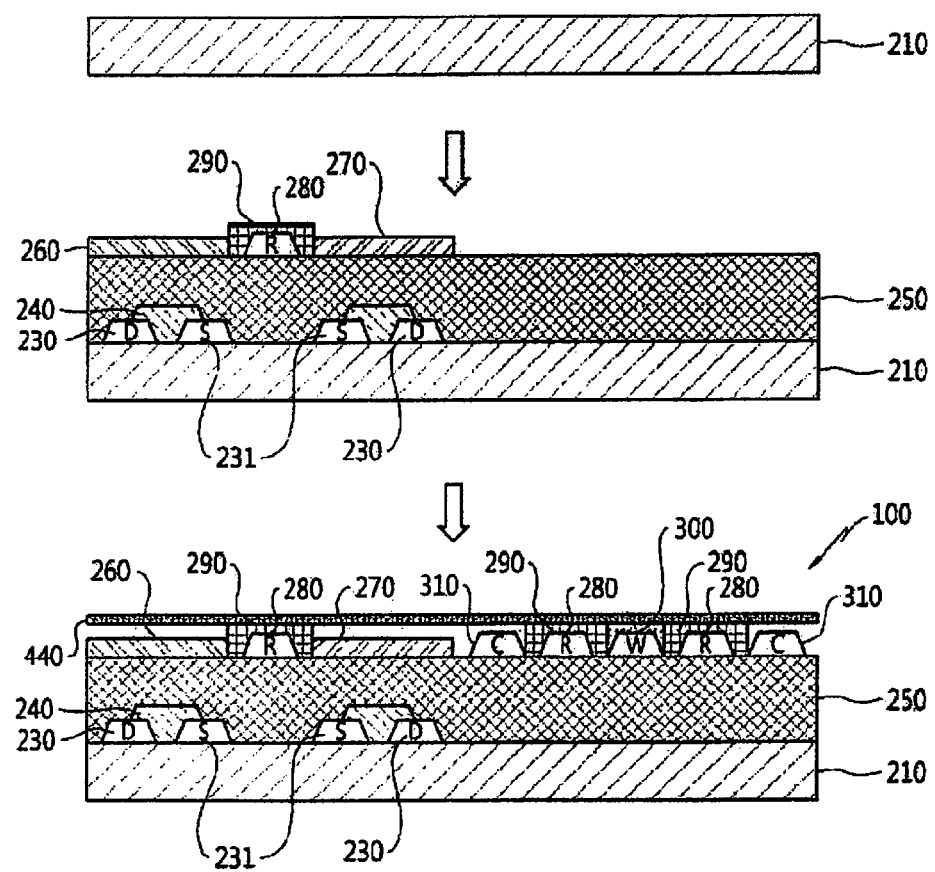
FIG. 3 is a schematic diagram illustrating an example of a process for manufacturing a cell-based transparent sensor.

FIG. 3 is a schematic diagram illustrating an example of a process for manufacturing the transparent cell-based sensor according to one general aspect.

Hereinafter, a method for manufacturing the cell-based transparent sensor will be described with reference to FIG. 3.

The Step 1 is a process of forming an ion-selective field effect transistor (ISFET) sensor on a transparent substrate 210.

First, a transparent substrate 210 is prepared by being cleaned using acetone, alcohol, and distilled water. A glass substrate or a transparent plastic substrate may be used as the transparent substrate 210, but the material for the substrate is not limited thereto.

Thereafter, a transparent electrode layer may be formed on the transparent substrate 210. A transparent metal oxide, a conductive polymer, a nano material, or a mixture thereof may be coated on the transparent substrate 210 to form the transparent electrode layer.

Materials used as the transparent metal oxide, the conductive polymer, and the nano material may include the materials previously described in the cell-based transparent sensor.

The transparent electrode layer may be patterned to form a transparent drain electrode 230 and a transparent source electrode 231. The method of forming the transparent drain electrode 230 and the transparent source electrode 231 by patterning the transparent electrode layer may be divided into two methods.

In a first method, a transparent metal oxide such as ITO may be selectively deposited through a lift-off process using a photolithograph method or using a shadow mask to form the transparent drain and source electrodes 230 and 231, or a printing process such as inkjet printing or screen printing may be performed on the conductive polymer, the nano material, or a composite material thereof to form the transparent drain and source electrodes 230 and 231.

In a second method, a wet etching or dry etching process may be performed on the transparent metal oxide deposited through a vapor deposition method to form the transparent drain and source electrodes 230 and 231.

In an example in accordance with a general aspect, an organic and inorganic transparent thin film may be further formed to improve adhesive properties of the transparent substrate 210 and the transparent drain and source electrodes 230 and 231 before the transparent electrode layer is formed on the transparent substrate 210.

Thereafter, a transparent semiconductor layer 240 may be deposited between the transparent drain and source electrodes 230 and 231 through the photolithograph method or the shadow mask method. Here, as described above with respect to the cell-based transparent sensor, the transparent semiconductor layer 240 may be an organic semiconductor such as pentacene. In another example, an inorganic semiconductor material such as ZnO or InGaZnO may be deposited to form the transparent semiconductor layer 240.

Next, a transparent ion-sensitive insulator detection layer 250 may be formed after the transparent semiconductor layer 240 is formed between the transparent drain and source electrodes 230 and 231. The transparent ion-sensitive insulator detection layer 250 may be formed as a single layer to manufacture the ISFET sensor. In another example, to improve insulating properties, an organic insulator such as parylene, PVP, PVA, or PI may be coated, and then an ion-sensitive insulator may be coated on the organic insulator to form a transparent ion-sensitive insulator detection layer 250 having a two layer structure.

After the transparent ion-sensitive insulator detection layer 250 is formed, transparent ion-selective membranes 260 and 270 may be formed on the transparent ion-sensitive insulator detection layer 250. Two kinds of transparent ion-selective membranes 260 and 270 selected from a pH detection membrane, a $Ca^{2+}$ detection membrane, a $K^+$ detection membrane, a $Na^+$ detection membrane, and a $pCO_2$ detection membrane may be deposited on the transparent ion-sensitive insulator detection layer 250 through a printing process such as inkjet printing or screen printing. Here, materials of the pH detection membrane, the $Ca^{2+}$ detection membrane, the $K^+$ detection membrane, the $Na^+$ detection membrane, and the $pCO_2$ detection membrane may include the materials previously described with respect to the cell-based transparent sensor.

After the two kinds of transparent ion-selective membranes 260 and 270 are formed on the transparent ion-sensitive insulator detection layer 250, a reference electrode 280 may be formed between the two transparent ion-selective membranes 260 and 270 to manufacture an ion-selective field effect transistor (ISFET) sensor. The reference electrode 280 may be manufactured as a silver-silver chloride reference electrode by selectively depositing a metal layer using a shadow mask and chlorinating the deposited metal layer through a wet or dry etching method. Thereafter, to improve the stability of the reference electrode 280, a polyvinylchloride (PVC) membrane 290 may be selectively formed through the inkjet printing method.

The Step 2 is a process of forming an oxygen detection electrochemical sensor in parallel to the ISFET sensor after the ISFET sensor is formed as described above.

That is, after the ISFET sensor is formed, a transparent counter electrode 310, the reference electrode 280, and a transparent working electrode 300 may be formed on the transparent ion-sensitive insulator detection layer 250, which is formed when the ISFET sensor is manufactured, through the shadow mask method in parallel to the ISFET sensor. Then, an oxygen detection membrane 230 may be formed on the working electrode 300 through the printing process to manufacture the oxygen detection electrochemical sensor.

As described above, the ISFET sensor and the oxygen detection electrochemical sensor are successively formed on the transparent substrate 210, and then a scaffold 440 for culturing cells and a well 410 may be formed on the ISFET sensor and the oxygen detection electrochemical sensor.

FIG. 4 is a cross-sectional view of an example of a cell-based transparent sensor manufactured according to one general aspect.

Referring to FIG. 4, a specific cell 420 to be measured using the cell-based transparent sensor according to the general aspect is cultured on a surface of the scaffold 440 within a cultivation solution 430. Thereafter, an analysis process may be performed according to an object to be analyzed such as a cytotoxic immune analysis with respect to specific drugs to optically measure cell metabolism and cell behavior phenomenon.

The cell-based transparent sensor may allow the optical observation of cell behaviors in real-time because the cell-based transparent sensor is formed of a transparent material. Also, a change in cell properties due to an environmental condition may be confirmed according to a variation in a current value generated by a concentration gradient change of $H^+$ (pH), $K^+$, $Ca^{2+}$, $Na^+$, $CO_2$ ($pCO_2$), and $O^{2-}$ (or $O_2$) depending on a cell metabolism change in the oxygen detection electrochemical sensor and the ISFET sensor.

Also, the present disclosure relates to a multi-detection sensor chip that includes a cell-based transparent sensor and a read-out conditioning circuit. The multi-detection sensor chip may be configured to optically and electrochemically measure cell behavior. The multi-detection sensor chip may include: a transparent substrate; an ISFET sensor disposed on the transparent substrate; and an oxygen detection electrochemical sensor disposed parallel to the ISFET sensor, wherein the read-out conditioning circuit conditions an electrical signal transmitted from the cell-based transparent sensor.

Figure 5:
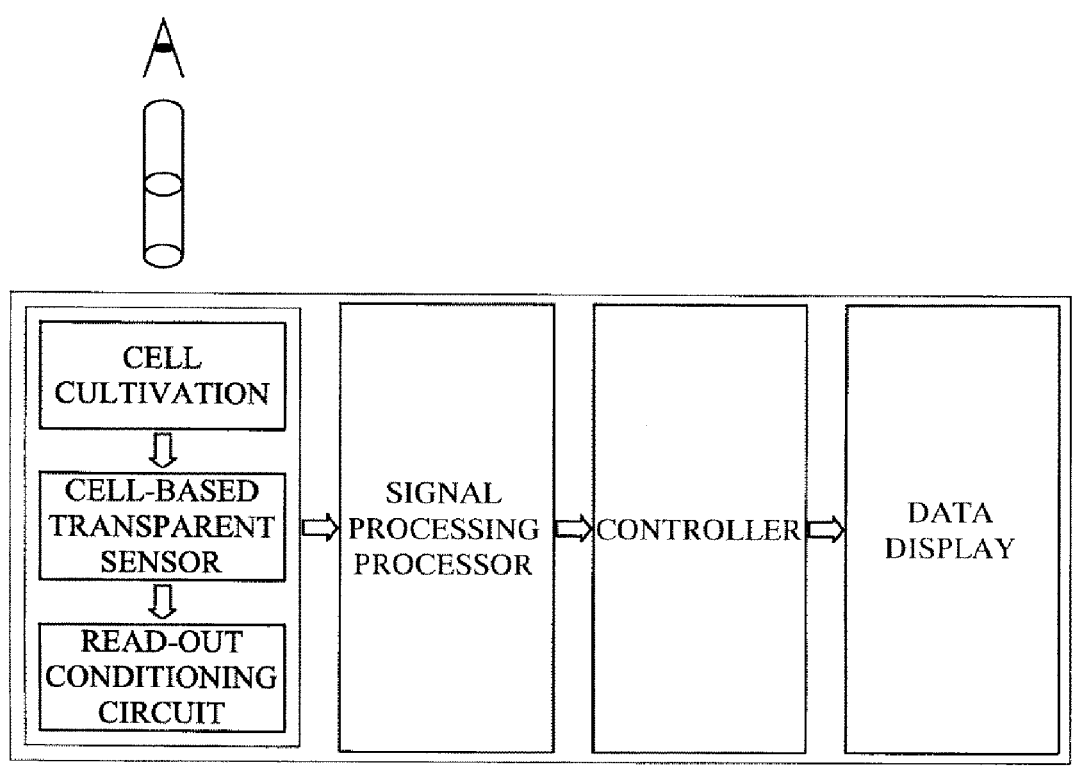
FIG. 5 is a schematic diagram illustrating a state in which an example of a multi-detection sensor chip is connected to a signal processing processor, a controller, and a data display.

FIG. 5 is a schematic diagram illustrating a state in which a multi-detection sensor chip is connected to a signal processing processor, a controller, and a data display according to one general aspect.

Referring to FIG. 5, a multi-detection sensor chip according to the general aspect is manufactured by integrating a cell-based transparent sensor and a read-out conditioning sensor on one transparent substrate.

The cell-based transparent sensor may be formed of the same material as described above to allow the optical observation of cell behavior in real-time.

The cell-based transparent sensor may convert a variation in a charge generated by the cell behavior into an electrical signal to transmit the electrical signal to the read-out conditioning circuit. The read-out conditioning circuit may amplify, filter, impedance-match, and modulate the electrical signal transmitted from the cell-based transparent sensor to transmit the conditioned signal to a processor.

The electrical signal transmitted from the read-out conditioning circuit may be converted into a digital signal by a signal processing processor. Thereafter, the digital signal may be transmitted to a data display device according a command of a control circuit and then be displayed through the data display device.

As described above, since the multi-detection sensor chip according to the general aspect is manufactured by integrating the cell-based transparent sensor and the read-out conditioning sensor on one transparent substrate, the cell behavior may be optically observed in real-time, and also the signal generated in the cell-based transparent sensor may be electrochemically detected.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A cell-based transparent sensor comprising:
    a transparent substrate;
    an ion-selective field effect transistor sensor disposed on the transparent substrate; and
    an oxygen detection electrochemical sensor disposed on the transparent substrate in parallel to the ion-selective field effect transistor sensor,
    wherein the ion-selective field effect transistor sensor comprises:
    transparent drain and source electrodes disposed on the transparent substrate;
    a transparent semiconductor layer disposed on the transparent drain and source electrodes;
    a transparent ion-sensitive insulator detection layer disposed on the transparent substrate, such that the transparent substrate, the drain and source electrodes, the transparent semiconductor layer and the transparent ion-sensitive insulator detection layer are disposed in that order;
    transparent ion-selective membranes disposed on the transparent ion-sensitive insulator detection layer; and
    a reference electrode disposed between the transparent ion-selective membranes, and
    the oxygen detection electrochemical sensor comprises a transparent counter electrode, the reference electrode, and a transparent working electrode which are disposed on the transparent ion-sensitive insulator detection layer.

2. The cell-based transparent sensor of claim 1, wherein each of the transparent drain and source electrodes is formed of a transparent metal oxide, a conductive polymer, a nano material, or a mixture thereof.

3. The cell-based transparent sensor of claim 2, wherein the transparent metal oxide comprises a transparent metal oxide selected from the group consisting of ITO, ZnO, IZO, AZO, ZTO, and $TiO_2$.

4. The cell-based transparent sensor of claim 2, wherein the conductive polymer is selected from the group consisting of polyaniline, polypyrrole, and poly(3,4-ethylenedioxythiophene).

5. The cell-based transparent sensor of claim 2, wherein the nano material is selected from the group consisting of graphene, carbon nanotube (CNT), and nanowire.

6. The cell-based transparent sensor of claim 1, wherein the transparent semiconductor layer is formed of a semiconductor material selected from the group consisting of pentacene, ZnO, and InGaZnO.

7. The cell-based transparent sensor of claim 1, wherein the transparent ion-sensitive insulator detection layer is manufactured by depositing a material selected from the group consisting of $Ta_2O_5$, $Al_2O_3$, $Si_3N_4$, and $SiO_2$ on the transparent substrate.

8. The cell-based transparent sensor of claim 1, wherein each of the transparent ion-selective membranes is selected from the group consisting of a pH detection membrane, a $Ca^{2+}$ detection membrane, a $K^+$ detection membrane, a $Na^+$ detection membrane, and a $pCO_2$ detection membrane.

9. The cell-based transparent sensor of claim 8, wherein, in the transparent ion-selective membranes, the pH detection membrane is coated with a material selected from the group consisting of tridodecylamine, nonadecylpyridine, octadecylisonicotinate, dipropylaminoazobenzene derivative, nile blue derivative, o-nitrophenyl octyl ether, and potassium tetrakis(p-chlorophenyl)borate (KTFPB); the $Ca^{2+}$ detection membrane is coated with a material selected from the group consisting of ETH 1001™ ((−)-(R,R)—N,N'-[bis(11-ethoxycarbonyl)undecyl-N,N',4,5-tetramethyl]-3,6-dioxaoctancediamide), ETH 129™ (N,N,N',N'-tetracyclohexyl-3-oxapentanediamide), K23EI (4,16-Di-N-octadecylcarbamoyl-3-oxabutyryl-1,7,10,13,19-pentaoxa-4,16-diazacycloheneicosane), bis(phenylazonaphthyl)tri-ether, and di(octylphenyl)phosphoric acid; the $K^+$ detection membrane is coated with a material selected from the group consisting of Bis(benzo-15-crown-5), Calix[4]arenecrown-5, functionalized polysiloxanes, KTTFPB™ (potassium tetrakis [3,5]-bis(trifluoromethyl)phenylborate), and poly-HEMA; and the $Na^+$ detection membrane is coated with a material selected from the group consisting of 16-Crown-5 and Calix[4]arenecrown-4; and the $pCO_2$ detection membrane is coated with a material selected from the group consisting of silicon rubber, microporous polypropylene, and microporous fluorinated polymer.

10. The cell-based transparent sensor of claim 1, wherein each of the transparent counter electrode and the transparent working electrode of the oxygen detection electrochemical sensor is formed of a material selected from the group consisting of carbon nanotube, graphene/hydroxyapatite, bromoform, polyethylene, and mixtures thereof; the reference electrode comprises a silver-silver chloride reference electrode in which silver is deposited and chlorinated; and a polyvinylchloride (PVC) membrane is disposed on the silver-silver chloride reference electrode.

11. The cell-based transparent sensor of claim 1, wherein the transparent substrate comprises a glass substrate or a transparent plastic substrate.

12. The cell-based transparent sensor of claim 1, wherein a well and scaffold for culturing cells are disposed on the cell-based transparent sensor.

13. A multi-detection sensor chip comprising the cell-based transparent sensor of claim 1 and a read-out conditioning circuit to optically and electrochemically measure cell behavior, wherein the read-out conditioning circuit conditions an electrical signal transmitted from the cell-based transparent sensor.

14. The multi-detection sensor chip of claim 13, wherein the read-out conditioning circuit is electrically connected to a signal processing processor, a controller, and a data display.

15. A cell-based transparent sensor comprising:
    a transparent substrate;
    a first ion-selective field effect transistor sensor and a first oxygen detection electrochemical sensor disposed on the transparent substrate; and
    a second ion-selective field effect transistor sensor and a second oxygen electrochemical sensor disposed on the transparent substrate, wherein the first and second ion-selective field effect transistor sensor comprise:

transparent drain and source electrodes disposed on the transparent substrate;

a transparent semiconductor layer disposed on the transparent drain and source electrodes;

a transparent ion-sensitive insulator detection layer disposed on the transparent substrate, such that the transparent substrate, the drain and source electrodes, the transparent semiconductor layer and the transparent ion-sensitive insulator detection layer are disposed in that order;

transparent ion-selective membranes disposed on the transparent ion-sensitive insulator detection layer; and a reference electrode disposed between the transparent ion-selective membranes, and the first and second oxygen detection electrochemical sensors comprise:

a transparent counter electrode, the reference electrode, and a transparent working electrode which are disposed on the transparent ion-sensitive insulator detection layer.

* * * * *